United States Patent [19]

Hester et al.

[11] Patent Number: 4,495,796

[45] Date of Patent: Jan. 29, 1985

[54] APPARATUS AND METHOD FOR MEASURING PERMEABILITY OF A MOVING WEB

[75] Inventors: Benny L. Hester; William F. Fleming, III, both of Winston-Salem, N.C.

[73] Assignee: R. J. Reynolds Tobacco Company, Winston-Salem, N.C.

[21] Appl. No.: 436,239

[22] Filed: Oct. 25, 1982

[51] Int. Cl.³ ............................................. G01N 15/08
[52] U.S. Cl. ............................................ 73/38; 73/37.7
[58] Field of Search .................................... 73/38, 37.7

[56] References Cited

U.S. PATENT DOCUMENTS

| 3,466,925 | 9/1969 | Ziegenhagen et al. | 73/38 |
| 3,720,095 | 3/1973 | Molins | 73/38 |
| 4,198,853 | 4/1980 | Graham et al. | 73/38 |
| 4,198,854 | 4/1980 | Washington et al. | 73/38 |
| 4,246,775 | 1/1981 | Stultz | 73/38 |
| 4,253,010 | 2/1981 | Brown et al. | 73/38 X |

Primary Examiner—Gerald Goldberg
Assistant Examiner—Joseph W. Roskos
Attorney, Agent, or Firm—Joseph E. Root, III

[57] ABSTRACT

The permeability of a moving web, for example, of perforated cigarette tipping paper, is monitored by inducing a fluid flow across the web, measuring the pressure drop across the web, independently measuring the volumetric flow rate, and calculating the permeability in CORESTA units. This method is embodied in apparatus which sequentially measures the instantaneous permeability of successive areas on the web to provide direct indication of the instantaneous CORESTA permeability.

14 Claims, 8 Drawing Figures

APPARATUS AND METHOD FOR MEASURING PERMEABILITY OF A MOVING WEB

BACKGROUND OF THE INVENTION

This invention relates to measurement apparatus and methods, and more particularly to apparatus and methods for measuring permeability of cigarette papers in terms of CORESTA units.

The papermaking art long has appreciated the need for monitoring the degree to which a paper product is permeable to air. For relatively impermeable products, void or hole detectors which pneumatically sense the presence of such imperfections and automatically deactivate the manufacturing apparatus until the problem can be solved are sufficient. A more accurate apparatus was disclosed by Ziegenhagen in U.S. Pat. No. 3,466,925. In this apparatus, a constant vacuum source is connected to a sensing head in contact with the moving paper web. A transducer in the vacuum line senses differentials in pressure, and feeds a signal to a strip recorder, where a capacitor averages the signal. Because changes in permeability cause changes in the flow rate of air in the vacuum line, and thus changes in pressure, the average signal recorded is roughly proportional to the permeability.

Paper permeability has become increasingly important to the cigarette industry with the advent of air dilution as a primary means of controlling particulate delivery. In comparison to the pre-existing situation, cigarette manufacturers now need to measure permeability over much wider ranges than before, and they need to conduct such measurements with greater accuracy in order to insure uniformity of the end product. In order to standardize measurement techniques, the cigarette industry has adopted a standard unit of measurement, called the CORESTA unit, based upon the volume of air passing through a unit area at a predetermined pressure per unit of time. One CORESTA unit is defined as one cubic centimeter of air passing through one square centimeter of paper, driven by a pressure of one centibar.

This unit of measure is applied to all the various types of paper used in the cigarette industry. Principally, these papers include highly porous plug wrap used in the formation of filter plugs, tobacco rod wrapper of various levels of permeability, and tipping paper. The latter, which is the paper used to wrap the filter plug and join it to the tobacco rod, presents a particular problem, when used in the form of ventilated tipping paper having minute perforations to provide air dilution. Such perforations are often microscopic in size, formed by mechanical, electrostatic, or laser perforating devices. The perforated region of the tipping paper is highly porous, but variations in the performance of the perforating apparatus will cause the permeability to vary greatly. For example, assume a tipping paper perforating apparatus running at normal production speed of 500 feet per minute. If this apparatus malfunctions so that a five-foot strip of tipping paper receives no perforations whatsoever, an on-line monitoring device would sense an instantaneous change in permeabilty from a level on the order of several thousand CORESTA units to zero CORESTA and back again in less than a second. Thus, any successful online monitoring device must be capable of dealing with wide, rapid swings in permeability.

This problem is further compounded by the discovery that the relationship between airflow through a paper web and the pressure differential across the web is nonlinear. Graham, in U.S. Pat. No. 4,198,853, which disclosure is hereby incorporated by reference herein, studied the phenomenon of airflow through a paper web and found that $V=A(PD)^N$, where V is the volumetric flow rate, and PD is the pressure differential across the web, A and N are constants for each paper but vary from paper to paper depending on the permeability. From this fact, it follows that adaptations of the Ziegenhagen device will be inherently inaccurate, especially over wide ranges of permeabilty. That device depends upon an assumed linear relation between flow and pressure. In other words, Ziegenhagen assumes that a given change in flow always results in the same change in pressure; as Graham shows, this supposition simply is not true. If permeability variations are sufficiently small that the relation approximates linearity, or if accuracy requirements are not high, the device may still serve. In the cigarette industry, however, paper permeability will vary greatly, and a high degree of accuracy must be maintained.

One solution to this problem would be to maintain either flow rate or pressure differential constant, allowing direct measurement of the other variable. Both Molins, U.S. Pat. No. 3,720,095 and Stulz, U.S. Pat. No. 4,246,775 disclose on-line permeability monitoring devices wherein the pressure drop (in the former) or the flow rate (in the latter) are set at constant values. Such devices, however, inherently are incapable of dealing with wide, rapid variation in permeability. The Stultz device, for example, calls for a constant flow rate, set with a metering valve. A transducer then monitors changes in pressure, which are taken to be directly related to changes in permeability. In practice though, the flow rate will not remain constant. Faced with a sudden, wide fluctuation in permeability, the flow rate must react, the metering valve notwithstanding. When the flow rate varies, Graham teaches that changes in pressure no longer bear a linear relation to changes in permeability, rendering the Stultz device inherently inaccurate. Exactly the same reasoning applies to the Molins disclosure.

Accurate measurement in CORESTA units is possible, but only by sacrificing on-line capability. Graham discloses a method for testing a paper web in terms of CORESTA units, but this method requires iterative computer analysis of data obtained by first varying pressure while measuring flow rate, and then varying flow rate while measuring pressure. Computer analysis defines the resulting flow rate/pressure curve. Another method is disclosed in U.S. Pat. No. 4,198,854, to Washington. This disclosure teaches that one may measure the CORESTA permeabilty of a paper web by directing a plurality of medium flows at different volumetric flow rates through the web, measuring changes in pressure. Again, computer analysis of the resulting data enables one to calculate the permeability. Obviously, iterative methods such as these inherently are incapable of providing instantaneous monitoring of a paper web moving at 500 feet per minute.

A disclosure by Brown, U.S. Pat. No. 4,253,010, is a reference-type permeabilty detector and control system. A vacuum source, regulated for constant flow, is connected to sensing means at two points, a reference point and a sample point. A U-shaped manometer tube is located between these vacuum lines, so that when the sensed permeabilty at the two points is equal, the vacuum line pressures are equal, causing the fluid in each leg of the U to be at the same level. Differences in permeability, and hence pressure, cause one leg or the other of the U to be at a higher level than the other, which condition is sensed by photoelectric means. This disclosure is incapable of solving the problem of accurate, direct readout of CORESTA permeabilty. First, this is a reference-type monitor, not adapted to provide output in terms of the CORESA permeability. Second, this disclosure shares with the patents discussed above the inherent inaccuracies of a constant-flow regulated system. Finally, detection of pressure differentials by means of a fluid manometer cannot respond to rapid variations in pressure. The mass of the fluid possesses sufficient inertia to damp out rapid variations, allowing measurement only of average, rather than instantaneous, values.

Thus, one who seeks direct, accurate, on-line measure of CORESTA permeability looks in vain to the prior art. One can achieve accurate measurement, or one can achieve on-line measurement; one cannot do both.

SUMMARY OF THE INVENTION

It is therefore an object of the present invention to provide a method and apparatus for measurement of the permeability of a moving web.

A further object of this invention is to provide a method and apparatus for the on-line measurement of the permeability, in CORESTA units, of a moving web of paper used in cigarette making.

It is a specific object of this invention to teach a method and apparatus for on-line CORESTA-unit permeability measurement of ventilated tipping paper used in cigarette manufacturing.

It is a further object of this invention to provide a method and apparatus for measuring cigarette paper permeability, capable of accurately measuring the instantaneous permeability of cigarette paper over a wide range of possible values.

It is also an object of the present invention to provide apparatus capable of sequentially measuring permeability at selected locations on a continuous moving web.

Another object of this invention is to enable a machine operator to monitor the permeability of a continuous moving web in terms of both average values and the range of values sensed.

Another object of this invention is to provide apparatus capable of monitoring the permeability of a wide variety of paper products used in the tobacco industry.

These and other objects are accomplished in the present invention by directly monitoring both the pressure drop and the flow rate of a fluid passing through a sensing head in contact with the moving web. The pressure differential across the web is monitored directly. The volumetric flow rate is determined by directing the fluid through a laminar flow element, sensing the pressure differential across the element, and developing a signal analogous to the flow rate. Calculating circuitry receives the flow rate and pressure drop signals as inputs and develops a signal directly proportional to the CORESTA value of permeability. LED display means allow a machine operator to monitor directly values of detected permeability, as well as the average value and the range of values.

The present invention includes means for monitoring the permeability of a continuous moving web at sequential locations on the web. Control means, responsive to a cam and cam roller, cause the head to traverse from an initial position, dwell in subsequent monitoring positions, and return to the initial position. At a point in the cycle when the head is not in contact with the web, the head and associated vacuum lines are purged of accumulated dust by a pulse of compressed air.

DETAILED DESCRIPTION OF A PREFERRED EMBODIMENT

Initially, it is helpful to consider the problem at hand in mathematical terms. The starting point is Graham's expression for gas flow through a permeable web: $V = A(PD)^N$, where V is volumetric flow rate, PD is pressure drop, and A and N are constants which vary from paper to paper. Using the subscript S to indicate values at CORESTA standard conditions and M to indicate measured values, the following relationships. obtain: $V_S = A(PD_S)^N$, and $V_M = A(PD_M)^N$. Thus, the ratio between CORESTA standard conditions and measured conditions can be expressed as follows: $V_S/V_M = A(PD_S)^N/A(PD_M)^N$. Obviously, the constant A drops out of this calculation. Solving for the CORESTA standard volumetric flow rate, and substituting the CORESTA standard pressure drop of 1.0 centibar, yields the following relationship: $V_S = V_M/(PD_M)^N$. Therefore, apparatus to provide direct CORESTA measurement of permeability must be able to measure the existing pressure drop, raise the pressure drop by the exponential factor N, measure the existing volumetric flow rate, and divide the latter by the former.

The following discussion addresses an embodiment of the present invention directed toward monitoring the permeability of a continuous web of ventilated tipping paper used in cigarette manufacturing. It should be understood, however, that this invention has a wide variety of other applications. With little modification, the apparatus disclosed could be employed elsewhere in the cigarette industry in monitoring the permeability of, for example, tobacco rod wrapper or the like. Similarly, those skilled in the art will appreciate the applicability of the present invention to any process wherein it is found desirable to monitor the permeability of a moving web.

Figure 1:
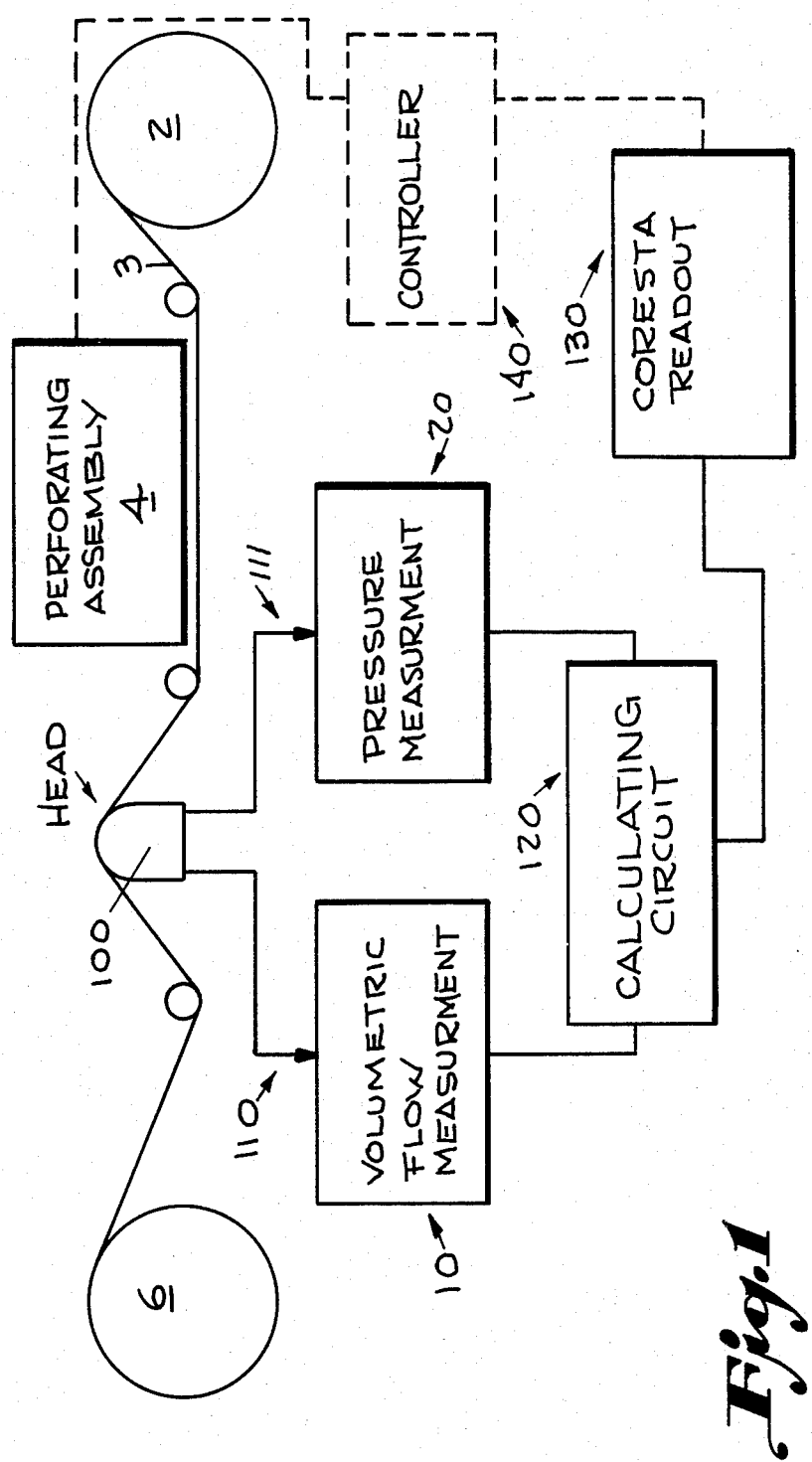
FIG. 1 is a schematic of the present invention.

Apparatus to accomplish this result is shown in general schematic form in FIG. 1. A permeable web 3 is fed from a feedroll 2, across a sensing head 100, to a take-up roll 6, which is driven by a power source (not shown). A perforating assembly 4 is located upstream of the pressure sensing head. This assembly is necessary if the permeable web consists of cigarette tipping paper but is of course not necessary if other materials, such as tobacco rod wrapper, were to be monitored. A fluid flow is established across the web, into sensing head 100, and through pneumatic line 110. Two independent measurement systems draw data from the sensing head. Pneumatic line 110 feeds a volumetric flow measurement system 10 which measures volumetric fluid flow and converts that measurement into an electrical signal. Similarly, a separate pneumatic line 111 feeds a pressure measurement system 20 which measures pressure drop across the web and converts that value into an electrical signal. Both signals are fed to a calculating circuit 120, which performs the mathematical operations required to convert measured values into a CORESTA value, and feeds that result to a CORESTA readout system 130. If direct feedback control of, for example, a perforating assembly, is desired, a controller 140, of a type known to the art, could be added to the system to provide such control.

Figure 2:
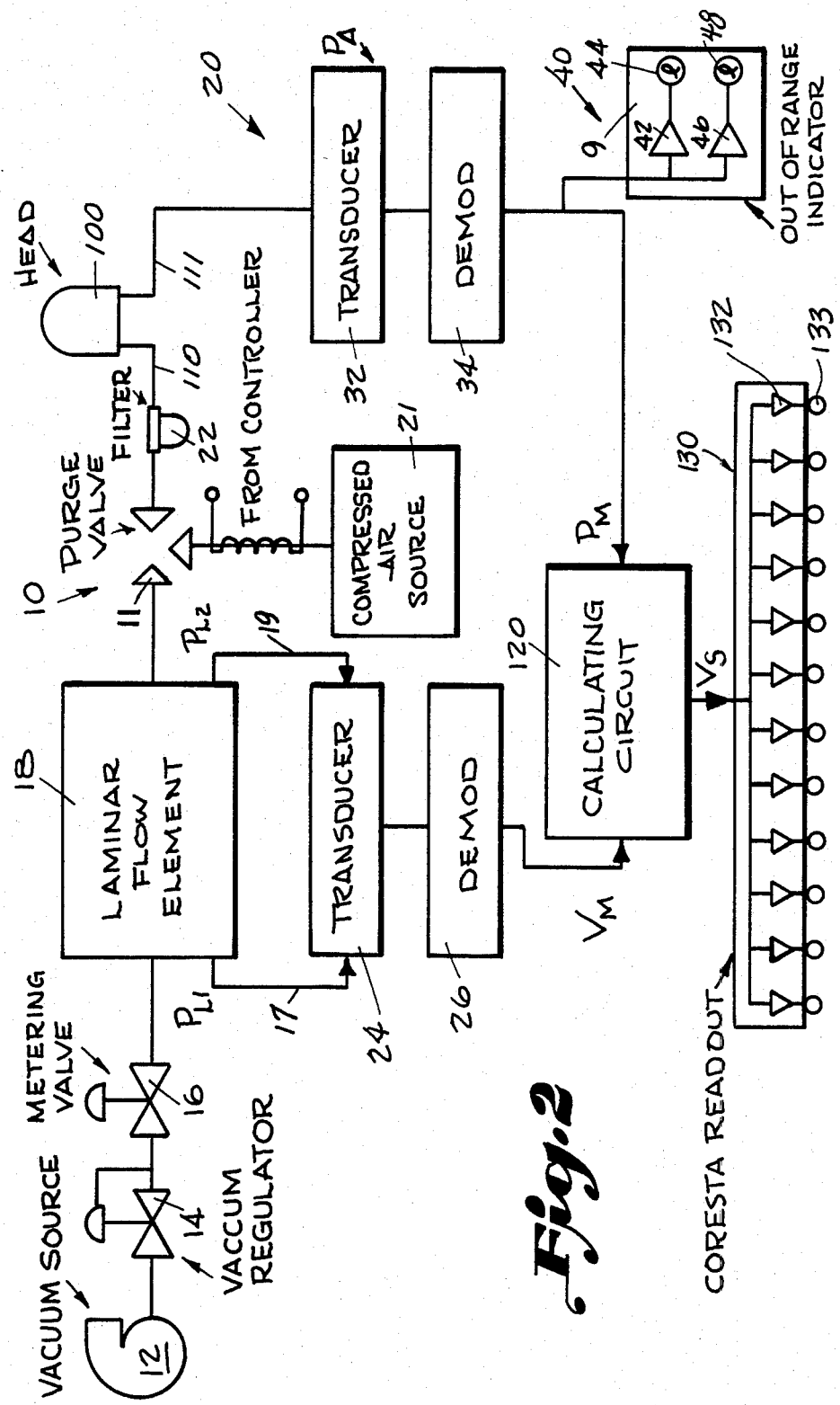
FIG. 2 is a detailed schematic of pneumatic and electronic measurement systems.

A detailed schematic of the measurement and readout systems is shown in FIG. 2. In the volumetric measurement system 10, airflow is established by a vacuum source 12, within parameters set by a vacuum regulator 14 and metering valve 16. These elements may be selected from the wide variety of suitable components available to the art.

Volumetric flow is measured in a laminar flow element 18. In this device, the fluid stream is directed through a matrix of minute parallel capillary passages whose cross section is sufficiently small to produce laminar flow from the normally occurring turbulent flow of the fluid stream. Under laminar flow conditions, volumetric flow rate is directly proportional to pressure drop, permitting direct, accurate measurement of volumetric flow. A suitable laminar flow element was found to be Model 50MJ10, manufactured by Meriam Instrument Division of Scott & Fetzer, 10920 Madison Ave., Cleveland, Ohio, 44102.

The pressure drop across the laminar flow element is obtained by coupling the element's inlet and outlet pressure sensing ports, $P_{L1}$ and $P_{L2}$, to the ports of a transducer 24 by pneumatic lines 17 and 19. The transducer converts the existing pressures to an electrical signal which, after demodulation in demodulator 26, corresponds to the measured volumetric flow rate, $V_M$. A suitable transducer and demodulator are Validyne models DP-15 and CD-101, respectively, produced by Validyne Engineering Corp., 8626 Wilbur Avenue, Northridge, Calif. 91324.

Directly upstream of the laminar flow element is a purge valve 11. This valve is a three-way device, whose normally-open ports are connected to the laminar flow element 18 and the vacuum line 110. The normally-closed port is connected to a compressed air source 21. This port is actuated by a solenoid responsive to a signal from the control system, as hereinafter explained. When the solenoid is actuated, the compressed air source is connected to vacuum line 110 and the volumetric measurement system 10 is disconnected. A filter 22 is located upstream of the purge valve and communicates directly with the pressure sensing head 100 by vacuum line 110. Both the filter and the purge valve may be selected from readily available components.

The pressure measurement system 20 communicates with the pressure sensing head via vacuum line 111. The pressure drop within the head is converted to an electrical signal by transducer 32, feeding demodulator 34. This signal is referenced to atmospheric pressure by leaving one of the transducer ports open to atmospheric pressure, $P_A$. Thus, the demodulator output signal corresponds to the measured pressure drop, $PD_M$. Suitable components for this transducer and demodulator are identical to those listed above.

As hereafter discussed, the value of the exponential constant N is experimentally determined for a given product and then set into the calculating circuit 120. As mentioned above, it is known that this constant also varies with changes in $PD_M$. We have discovered, however, that variations on the order of 10–20% do not sufficiently affect the value of N to render permeability measurements unacceptably inaccurate. We therefore provide an out-of-range indicator 40 to insure that the average pressure in the system stays within this operating range. That result is achieved by connecting two comparators 42 and 46 in parallel with the pressure drop signal demodulator 34 output. Through conventional resistive networks (not shown), the trigger points of these comparators are chosen such that one comparator triggers when the demodulator output falls below a preselected value corresponding to the low end of the operating range, and the other triggers when the demodulator output exceeds an upper limit. The comparator outputs are connected to lamps or LED's 43 and 45 to give the machine operator a visual indication of an out-of-range condition. The operator can then adjust metering valve 16 to bring the average pressure within operational limits. Of course, some conventional means of feedback control could be employed to accomplish the same result. Typical components for comparators 42 and 46 are Texas Instruments Type 339 comparators, readily available to the art. Resistive networks are chosen such that the lower limit comparator triggers at a signal corresponding to a pressure drop of 0.8 centibars, and the upper limit comparator triggers at values in excess of 1.2 centibars.

To summarize, the measurement systems operate as follows. A vacuum source 12 establishes fluid flow through the volumetric flow system 10, vacuum line 110, sensing head 100, and across the web 3. A metering valve 16 and vacuum regulator 14 cooperate to maintain pressure in this line at about 1.0 centibar. Pressure drop across a laminar flow element 18 is converted to an electrical signal analogous to the measured volumetric flow rate, $V_M$ by transducer 24 and demodulator 26. The exact pressure drop at the sensing head 100 is converted into an electrical signal corresponding to the measured pressure drop, $PD_M$ by transducer 32 and demodulator 34. An out-of-range indicator 40 insures that the system pressure remains within operating limits. At selected points in the measurement cycle, as discussed hereafter, the control system actuates the purge valve 20 solenoid, disconnecting the vacuum line 110 from the laminar flow element 18 and connecting it to a compressed air source 21. Compressed air then flows through the filter 22 and vacuum line 110, and out the monitoring head 100, discharging any dust which may have accumulated therein. Subsequently, the solenoid is deactivated and the vacuum line reconnected to the laminar flow element.

Figure 3:
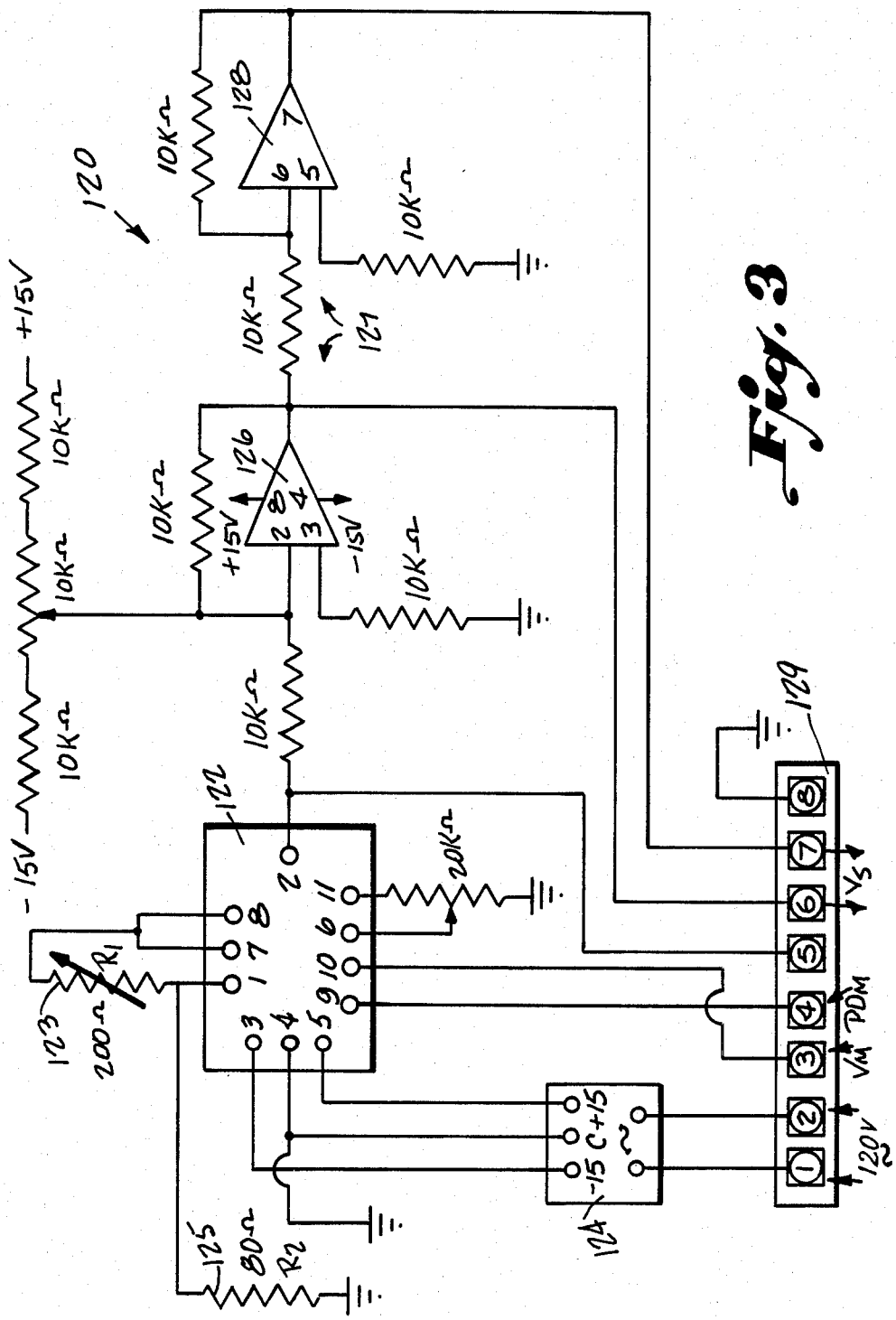
FIG. 3 is a schematic of a calculating circuit.

The signals $V_M$ and $PD_M$ are processed in the calculating circuit 120 to produce the CORESTA readout signal $V_S$, as shown in the schematic of FIG. 3. Mathematical processing takes place in a programmable multifunction module 122. Resistive values and pin connections shown correspond to those employed on Analog Devices model 433J, available from that company at Route 1, Industrial Park, Norwood, Mass., 02062. Signals $PD_M$ and $V_M$ are input through module pins 9 and 10 respectively. The potentiometer 129 connected across pins 6 and 11 establishes the module's zero point, and power requirements (plus 15 and minus 15 volts) are furnished at pins 3, 4, and 5. A conventional power supply 124 supplies these requirements from line voltage, but these voltages could be obtained from any suitable available source.

Module 122 is capable of performing a variety of mathematical operations. As here employed, it is programmed to solve the equation for volumetric flow rate at CORESTA standards. The value of the exponential constant N is determined by the values of the network comprising resistors 123 and 125 connected, at pins 1, 7, and 8. For a given paper, N is first determined experimentally by measuring volumetric flow rates at several different known pressures and solving Graham's equation for N. For example, perforated cigarette tipping paper was found to have a value of N equal to 0.53. As the module manufacturer explains, values for the resistor network are then chosen by the formula $N = R_2/R_1 + R_2$, $R_1$ being resistor 123 and $R_2$ resistor 125. Because it was desirable to enable the present invention to monitor permeability of a variety of papers having different values of N, resistor 123 ($R_1$) was chosen to be a potentiometer having a value of 200 ohms, in combination with a fixed resistor 125 ($R_2$) having a value of 80 ohms. This combination allows N to be selected within a range of values from zero to 0.71. This range has been found sufficient to cover all applications concerning cigarette papers. The particular value of N for a selected paper is first determined experimentally, and the corresponding resistance value for the potentiometer is indicated on the potentiometer dial. Alternatively, resistor 123 could be fixed if the device were to be employed to monitor only one type of paper. For example, an apparatus used only to monitor the permeability of perforated cigarette tipping paper could substitute a 70 ohm fixed resistor as resistor 123.

The module 122 output, $V_S$ is available at pin 2. This signal may be utilized directly, but we prefer to process it further in a two-stage operational amplifier 127, such as Motorola part No. MC1458. The processing required for the $V_S$ signal depends upon the input requirements of the meter, readout device, or control system which utilizes this signal as its input. The components chosen here produce an output signal tailored to the requirements of the CORESTA readout device 130, discussed below. Resistance and voltage values are conventional, and were chosen as shown in FIG. 3. The first stage 126 of operational amplifier 127 performs a scaling function, linearly increasing the signal level. The second stage 128 serves as a buffer, isolating the multi-function module output from the readout device.

Input to and output from the calculating circuit is accomplished through an 8-pin connector 129 or similar suitable device. Pins 1 and 2 are line voltage connections, and pin 8 is the ground connection. Connector pins 3 and 4 are the volumetric flow ($V_M$) and measured pressure drop ($PD_M$) inputs, respectively. Pin 5 provides a direct output signal from the multifunction module; this signal is useful also in setting the module zero point. Pins 6 and 7 provide the system output signal $V_S$. Any or all of these signals may be monitored, as desired, through conventional metering means known in the art.

Returning to FIG. 2, the calculating circuit output signal, $V_S$ is fed to CORESTA readout device 130. This device consists of a bank of comparators 132 connected in parallel, each of whose output drives an LED 133. Resistive networks associated with the comparators, as is conventionally known, establish comparator trigger points, corresponding to given levels of signal $V_S$. The number of comparators can be chosen as a matter of design choice based upon the discrimination desired in the readout unit.

Selection of the type readout device shown offers several advantages. It must be recognized that at operating speeds, individual perforations are passing over the pressure monitoring head at a rate of about 25,000 perforations per second. The limitations of the transducer and demodulator, however, limit the effective response time of the system to about 5,000 cycles per second. A conventional meter readout further would damp the response time to the point that only gross average values would be reflected. The system shown, however, insures that each reading corresponding to the minimum system response time results in the generation of a particular value of $V_S$, further resulting in the triggering of the corresponding comparator. Thus, over a short period of time, variations in $V_S$ will result in many comparators being triggered. The comparator corresponding to the average value of $V_S$ will be triggered often, resulting in its corresponding LED being perceived as glowing continuously and brightly. Other comparators in the range of sensed values will be triggered less frequently, and will be seen as glowing less brightly. At the limits of the sensed range, the corresponding LED's will be perceived as flickering. Thus, the operator sees not only the average value of web permeability, but also the range of values being sensed. This form of readout enables an operator to monitor the entire process, not merely the average value of permeabilty.

Figure 4:
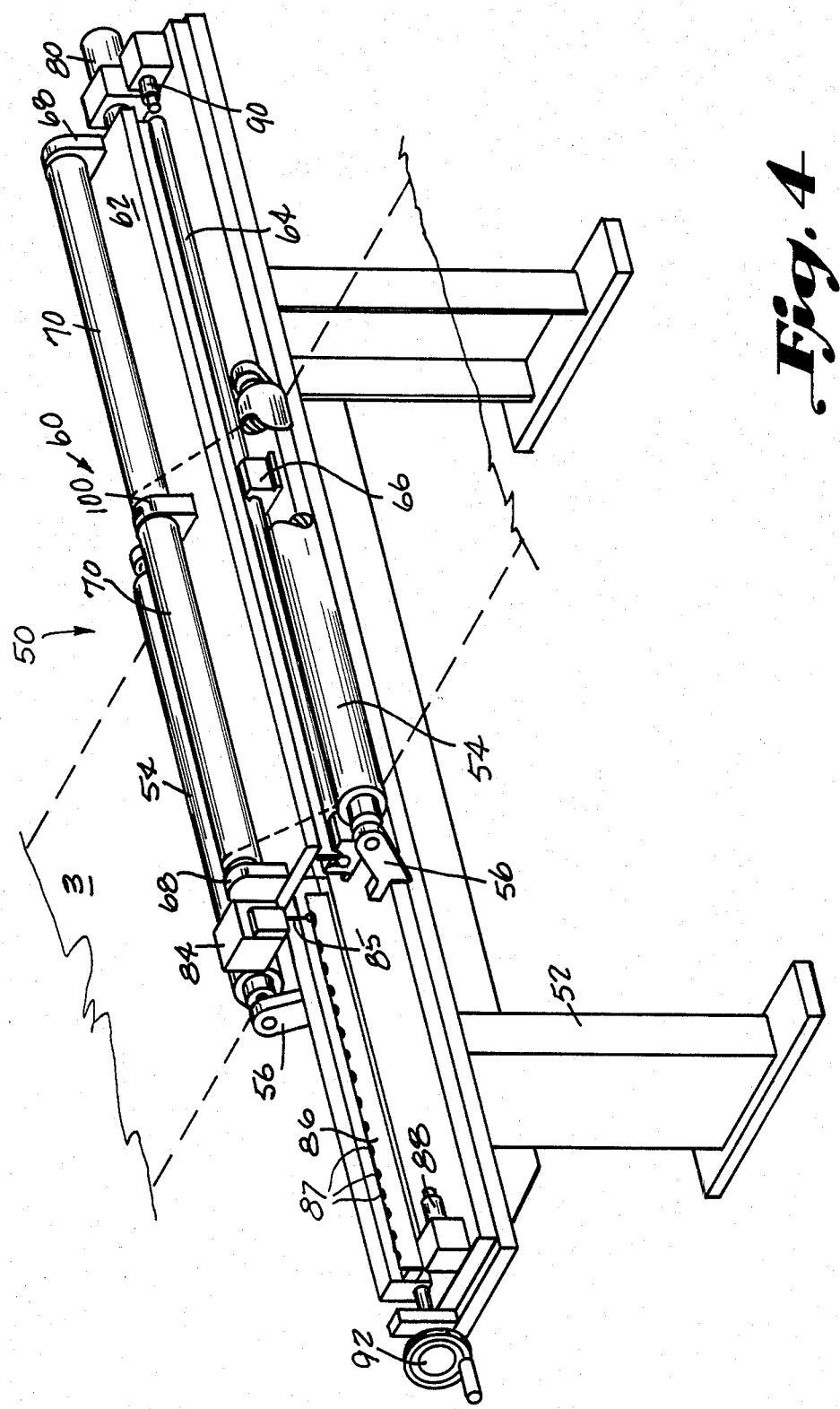
FIG. 4 is a perspective of a traversing head apparatus.
Figure 5:
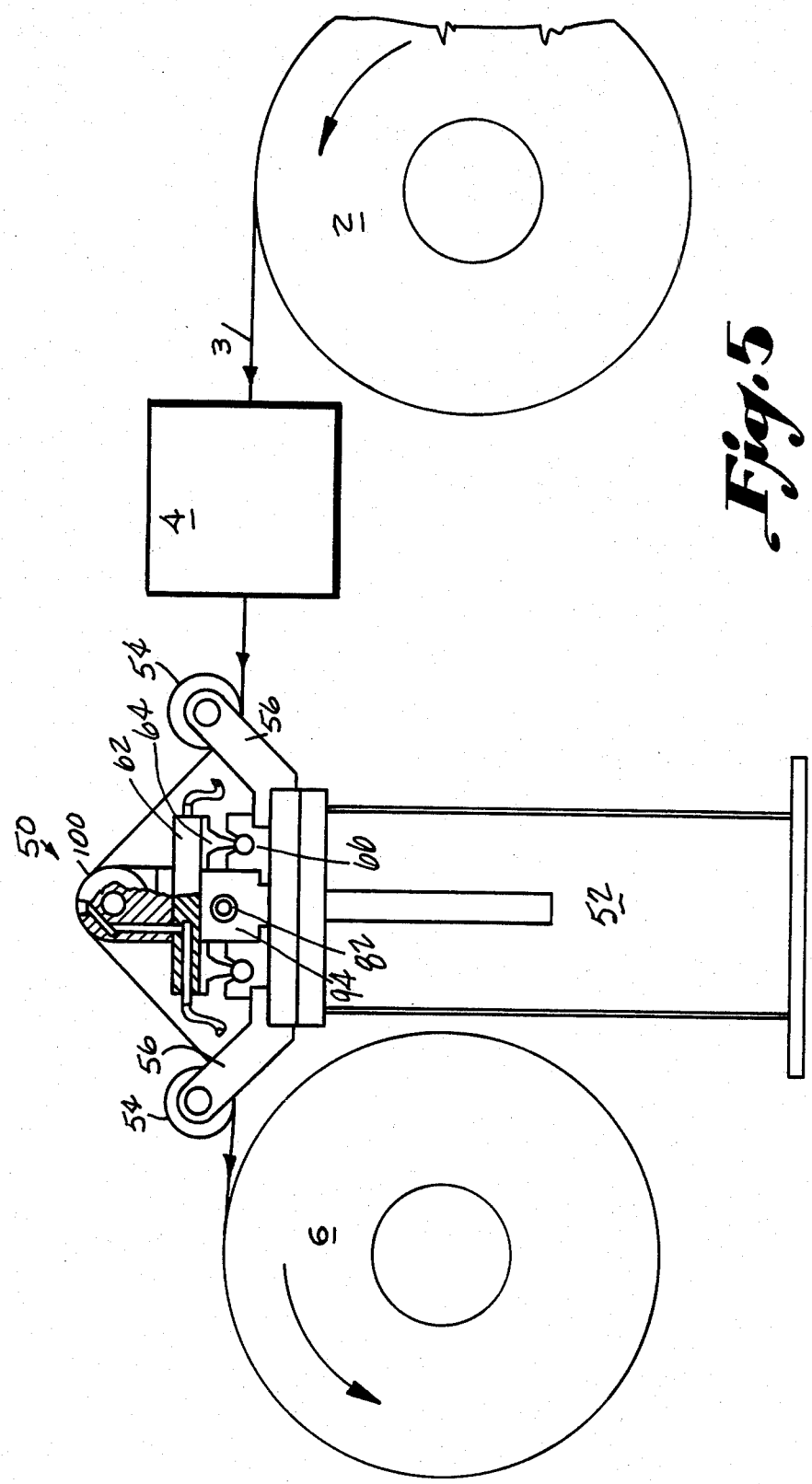
FIG. 5 is a side view of the traversing head apparatus.

The measurement and readout systems monitor the permeability of the continuous web through the action of sequential sensing apparatus 50, shown in FIGS. 4 and 5. The particular product which is to be monitored generally governs the selection of apparatus by which the measurement and readout systems are coupled to the web. The apparatus shown is adapted to monitoring perforated cigarette tipping paper, but those skilled in the art will appreciate that obvious modifications could be made to adapt it to other products, such as tobacco rod wrapper. Cigarette tipping paper normally is manufactured in a relatively wide web, which is later slit into individual ribbons of tipping paper. This paper is perforated so that each ribbon of tipping paper contains one band, row, or lane of perforations, formed in selected patterns by the perforating apparatus 4, shown in FIG. 1. Because the objective of monitoring the permeability of perforated tipping paper is to insure that the perforating apparatus performs effectively, each band of perforations must be monitored. Although it is possible to provide individual sensing means for each band, the present invention accomplishes the desired result by sequentially monitoring each perforation band.

The sequential sensing apparatus 50, generally comprises the sensing head 100, mounted on a traversing table assembly 60, which is carried on a base 52, and associated control and drive means (not shown). The base generally lies at right angles to the path of web travel. Mounted on base 52 are two rollers 54, suitably journaled for free rotation in supports 56, extending outwards and upwards from each side of the base. The rollers are positioned so that the web engages the underside of one roller, travels over the sensing head, engages the underside of the second roller, and feeds onto the take-up roll 6 (shown in FIG. 1).

The traversing table assembly 60 is mounted on the base by slides 64 which slide on blocks 66. As seen in FIG. 5, the slides are circular in cross section, and the slide blocks are adapted to engage them, but any suitable slide mechanism could be used for this mounting. The slides extend the length of the traversing table, and enable the table to move under the web from a start position, in which one end of the table is positioned under the web (seen in FIG. 4), to a finish position in which the other end of the table is under the web.

A plate 62 is carried on the slides 64, and sensing head 100 is mounted generally in the center of the plate. Head rollers 70 extend on either side of the head to head roller supports 68, mounted at the ends of the plate and suitably journaled for free rotation in both the head and the head roller supports. The roller diameter may be of any convenient dimension, and the roller surface should be selected to avoid marking the web. In the embodiment depicted, the rollers are fabricated of stainless steel and have a radius of curvature equal to that of the sensing head 100, discussed below.

Figure 6:
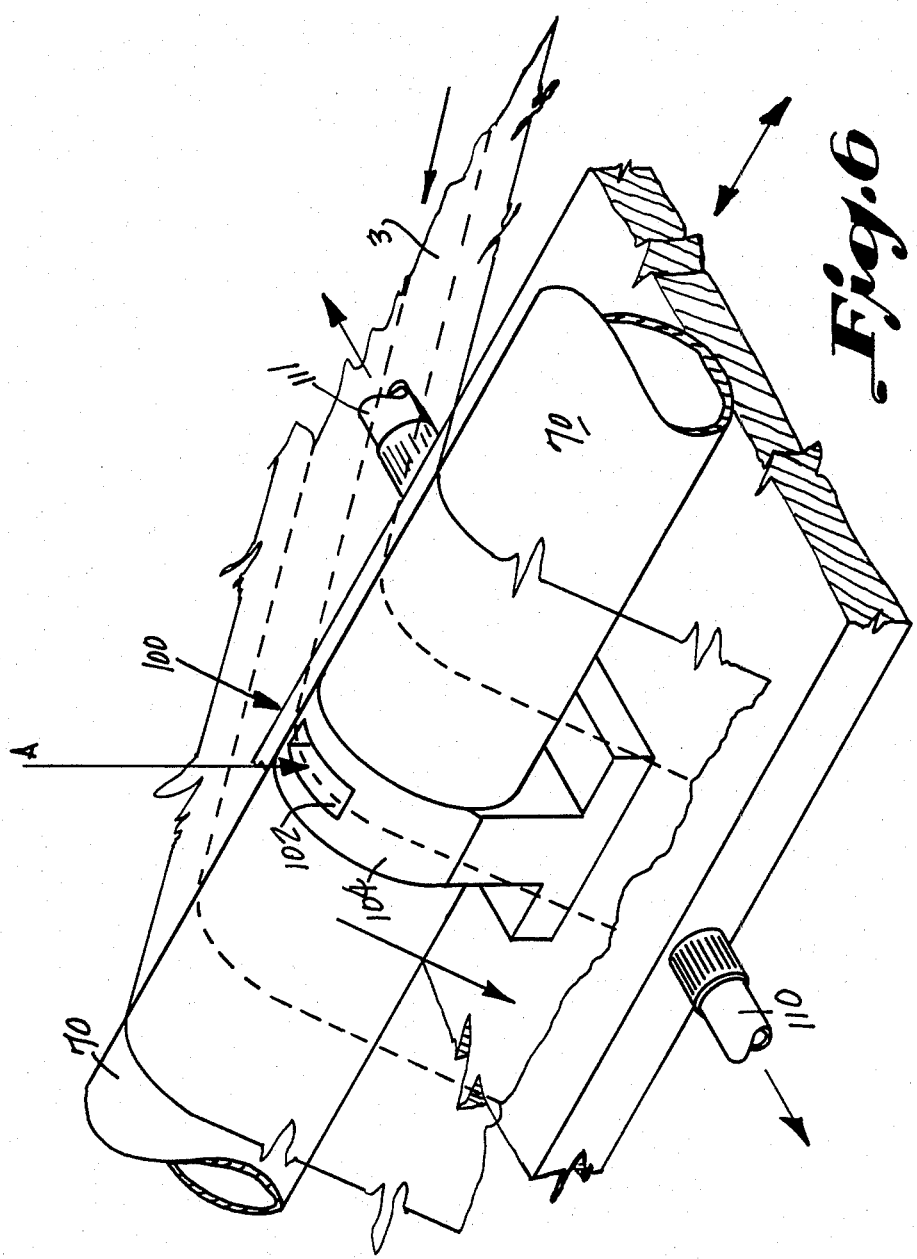
FIG. 6 is a detailed perspective of a pressure sensing head.
Figure 7:
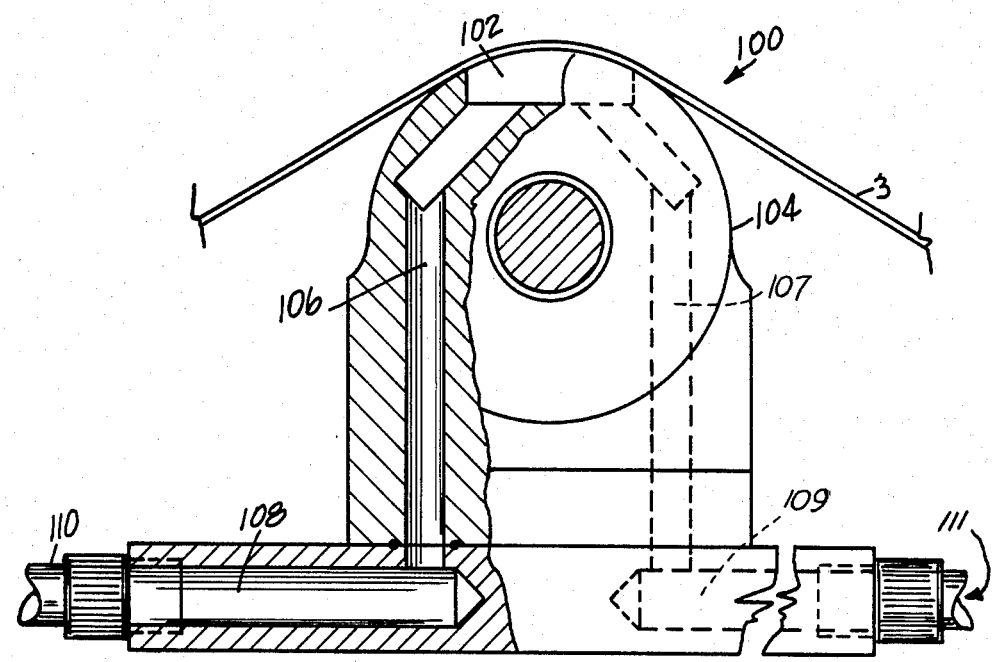
FIG. 7 is a side view of the pressure sensing head, partially broken away to show internal construction.

The sensing head 100, is fixed at approximately the center of the plate 62. The top portion of the head (FIGS. 6 and 7) has a semi-circular face 104, matching the curvature of head rollers 70. A slot 102 is formed at the apex of the head. Separate air passages 106 and 107 within the head communicate with the slot and passages 108 and 109 formed in the plate 62. Vacuum lines 110 and 111, joined to the plate passages 108 by suitable connector means, lead to the measurement systems discussed above.

The machining of the head is particularly critical. First, the face 104 must be absolutely smooth and flat, and rollers 70 must be mounted such that face 104 protrudes slightly above the rollers. These two requirements insure proper contact between the face and the web, so that air flows into the slot 102 (shown as Arrow A, FIG. 6) only through the web, without leakage around the sides. The cross-sectional area of the slot must be maintained within tight tolerances, so that volumetric flow rate can be calculated accurately. In the embodiment shown, the head face is fabricated within a tolerance of plus or minus 0.0005 inches (0.0127 mm), and the slot is machined to have a surface area of 0.25 square inches (50.41 square mm).

Returning to FIGS. 4 and 5, drive and control means cause the moving table assembly to travel from a start position, where the head is aligned with the right-most row of perforations (shown in FIG. 4), to an ending position, in which the head has traversed all the way across the web and the head has emerged beyond the left edge of the web. Movement is effected by a motor 80, driving a lead screw 82, which engages a threaded receiver 94 fixed to the underside of plate 62. Rotation of the lead screw causes the threaded receiver, and thus the plate, to move transversely across the web by sliding on blocks 66. A cam roller switch 84 is mounted at the end of plate 62 opposite to the motor. This switch is activated by a spring-loaded finger 85 having a roller at its tip. The roller engages detents 87 cut in a cam 86, mounted under the plate and parallel to its direction of movement. Adjustment of the cam back and forth along the plate's direction of travel to insure correct cam positioning is accomplished by adjustment wheel 92. In its start position, the plate engages return limit switch 90. At its finish position, at the other end of the base, the plate engages travel limit switch 88. A controller (not shown) regulates the interaction of these elements during an operational cycle, as hereinafter discussed.

Figure 8:
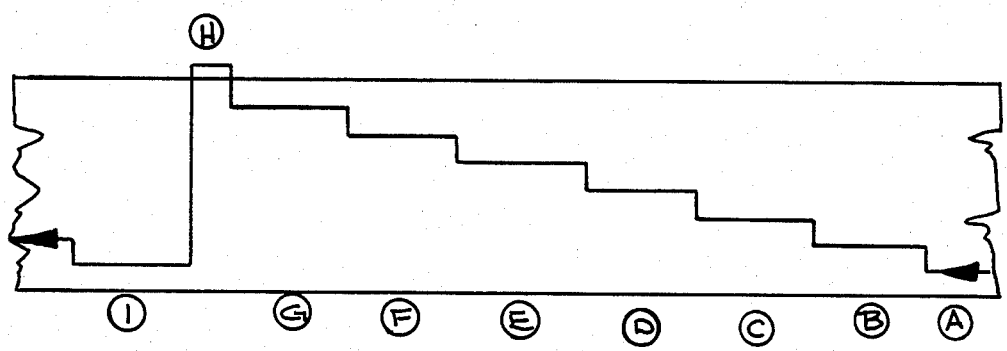
FIG. 8 is a schematic representation of the cyclic motion of the traversing head apparatus.

Operation of the apparatus is best understood with reference to FIGS. 4 and 8. The latter figure depicts a complete operational cycle of the apparatus in monitoring the permeability of a moving web of perforated tipping material. As previously mentioned, such webs are prepared in some multiple of a single tipping paper width. FIG. 8 depicts a typical web, which later will be slit into seven ribbons of tipping paper. Each such ribbon requires one row, or lane, of perforations. Therefore, the permeability monitoring apparatus must sequentially traverse to cover each of the seven lanes.

At the start of a cycle, the apparatus is in start position A (FIG. 8), monitoring the rightmost lane of perforations, as depicted in FIG. 4. During machine setup, adjustment wheel 92 is used to insure that the head is centered on this lane of perforations. After cycle initiation, the controller causes the apparatus to dwell in position A for a preselected time. Then, motor 80 is energized, causing the head to traverse inward to the next lane of perforations, at position B. It should be noted that head rollers 70 insure that the web is fully supported at all times. To minimize friction, the only non-rotating element in contact with the web is the head itself. The traversing assembly 60 continues to traverse toward position B until the spring-loaded finger 85 of cam roller switch 84 engages the succeeding detent 87 on cam 86. Detents are spaced on the cam according to the distribution of perforation lanes on the web; different cams can be fabricated to accommodate any pattern of lane distribution and can be substituted when changing product configuration. Thus, the apparatus is adaptable to any given spacing and pattern of perforation lanes. Engagement with the detent 87 causes the cam roller switch 84 to send a signal to the controller, which then stops the motor. The head dwells in position B for a preselected time, after which the controller reenergizes the motor, causing the apparatus to traverse to the next inward lane, at position C. This alternate traversing and dwelling continues until the apparatus reaches the end of the base, at position H, where the slide 64 makes contact with travel limit switch 88. Here, the head emerges from under the web, which is then completely supported by head roller 70. Energization of switch 88 causes the controller to initiate the purge cycle, discussed above, during which a pulse of high-pressure air is passed through the vacuum line and out the head, blowing out any dust which may have been drawn into the system during the monitoring phase. At the completion of the purge cycle, the controller energizes the motor in a reverse direction, causing the apparatus to traverse across the entire width of the web back to the initial position, position I, which is identical to position A. This action completes one cycle, and the controller automatically initiates another cycle, and so on.

An alternate approach to monitoring permeability would be to provide a separate monitoring head for each lane of perforations. That approach, however, poses serious drawbacks. Primarily, such an apparatus would be highly expensive. The monitoring heads are difficult to manufacture, as the slot and air passages must be fabricated to exacting tolerances. Also, inclusion of multiple heads would increase the friction imposed upon the web. Stationary heads could not be purged frequently, requiring loss in production time to accomplish this step, as well as the possibility of further losses in production time due to the system clogging. Furthermore, it is not necessary to accept these drawbacks, because it has been found that sampling the permeability of a perforation lane for given segments of the total running time furnishes an adequate control over finished product quality. The fraction of total running time available to monitor each lane is a function of the number of lanes to be monitored, and once that number is known, a dwell time can be selected sufficient to insure an adequate sample on each lane is taken during each cycle.

Other variations upon the method and apparatus herein disclosed are possible without departing from the spirit of the present invention. For example, the head shape and slot dimensions could be altered to fit the circumstances of a particular manufacturing operation. Likewise, electronic circuitry could be provided to allow for direct control of the perforating mechanism via a feedback loop from the measurement system. These and other variations, which will be appreciated by those having skill in the art, fall within the scope of the present invention.

We claim:

1. Apparatus for measuring the permeability of a continuous moving web, comprising:
   a sensing head assembly in contact with the web;
   means for directing a fluid flow through the web and said head;
   means for measuring the volumetric flow rate of said fluid flow and generating signals analogous thereto;
   means for measuring the pressure drop in said fluid flow across the web and generating signals analogous thereto, said pressure measurement simultaneous to and independent of said flow measurement;
   means for calculating the permeability of the web according to the formula:

$$\text{Permeability} = \frac{\text{Measured flow rate}}{\frac{\text{Measured pressure drop}^N}{\text{Standard pressure drop}^N}}$$

where N is a constant;
   means for communicating the results of said calculation as a permeability signal.

2. The apparatus of claim 1, wherein said flow measurement means includes:
   a laminar flow element; and
   means for sensing the pressure drop across said laminar flow element and developing signals analogous thereto.

3. The apparatus of claim 2, wherein said sensing head assembly includes:
   a sensing head in contact with the web, having a slot formed therein for conducting said fluid flow;
   means for non-frictionally supporting the portion of the web not in contact with said head mounted adjacent said head;
   means for traversing said head to multiple sensing location on the web.

4. The apparatus of claim 3, wherein said traversing means includes:
   a traversing table, moveably mounted transverse to the web;
   a cam mounted adjacent said table with means for indicating subsequent sensing locations;
   a cam roller travelling on said cam;
   means for sensing and communicating the engagement of said cam with said indicating means;
   means for controlling the traverse of said table.

5. The apparatus of claim 1, further comprising:
   means for periodically purging said head with fluid to remove accumulated dust.

6. The apparatus of claim 1, wherein said communicating means comprises:
   a plurality of comparators in parallel, each of said comparators responsive to a selected permeability signal level; and
   a plurality of light emitting devices, each of said devices responsive to the output of one of said comparators.

7. The apparatus of claim 1, 2, 3, 4, 5, or 6, wherein said measurements are made in CORESTA units of permeability.

8. A method for measuring the permeability of a continuous moving web, comprising the steps of:
   feeding a continuous web from a feed roller, across a sensing head in contact with the web, to a take-up roller;
   inducing a fluid flow through said web and said sensing head;
   determining the volumetric flow rate of said fluid flow and generating an electrical signal analogous to same;
   measuring the pressure drop across said web, independently of and simultaneously to said flow rate determination;
   calculating the permeability of the web in standard units from the formula;

$$\text{Permeability} = \frac{\text{Measured flow rate}}{\frac{\text{Measured pressure}^N}{\text{Standard pressure}^N}} \text{ ; and}$$

where N is a constant;
   communicating said calculated permeability.

9. The method of claim 8, further comprising the step of displaying the calculated permeability.

10. The method of claim 8, wherein said standard units are CORESTA permeability units.

11. The method of claim 8, wherein said determining step further includes:
    directing said fluid flow through means for producing laminar flow; and
    sensing the pressure drop across said laminar flow means.

12. The method of claim 8, further comprising the step of traversing said sensing head to multiple sensing locations on the web.

13. The method of claim 12, further comprising the step of purging the head of accumulated dust after a selected number of traversing steps.

14. The method of claims 12 or 13, wherein said traversing step includes sequentially dwelling at selected positions on the web.

* * * * *